(12) United States Patent
Bottlang et al.

(10) Patent No.: US 9,700,361 B2
(45) Date of Patent: Jul. 11, 2017

(54) BONE PLATE FOR ELASTIC OSTEOSYNTHESIS

(71) Applicant: Zimmer, Inc., Warsaw, IN (US)

(72) Inventors: Michael Bottlang, Happy Valley, OR (US); Steven M. Madey, West Linn, OR (US); Kyle Wirtz, Portland, OR (US); Stanley Tsai, Portland, OR (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/047,702

(22) Filed: Feb. 19, 2016

(65) Prior Publication Data

US 2016/0166293 A1    Jun. 16, 2016

Related U.S. Application Data

(63) Continuation of application No. 13/755,493, filed on Jan. 31, 2013, now Pat. No. 9,295,508.

(Continued)

(51) Int. Cl.
*A61B 17/80* (2006.01)
*A61B 90/00* (2016.01)

(52) U.S. Cl.
CPC ........ *A61B 17/8028* (2013.01); *A61B 17/808* (2013.01); *A61B 17/8047* (2013.01);
(Continued)

(58) Field of Classification Search
CPC ................... A61B 17/8004; A61B 17/8047
See application file for complete search history.

(56) References Cited

U.S. PATENT DOCUMENTS

| 2,406,832 A | 9/1946 | Hardinge |
| 2,580,821 A | 1/1952 | Toufick |

(Continued)

FOREIGN PATENT DOCUMENTS

| CN | 104135953 A | 11/2014 |
| EP | 0615728 A2 | 9/1994 |

(Continued)

OTHER PUBLICATIONS

"U.S. Appl. No. 14/308,286, Notice of Allowance mailed Mar. 23, 2016", 8 pgs.

(Continued)

*Primary Examiner* — Andrew Yang
(74) *Attorney, Agent, or Firm* — Schwegman Lundberg & Woessner, P.A.

(57) ABSTRACT

Embodiments provide a method and device for plate osteosynthesis of a bone fracture that allows angle-stable fixation of the bone fracture, while permitting elastic axial motion at the fracture site in a controlled, symmetric manner to stimulate fracture healing. Embodiments pertain to a bone plate having an outer surface and a bone-facing surface. The bone plate incorporating internal sliding elements containing a threaded receiving hole for bone screws that have a correspondingly threaded screw head. The sliding elements undergo controlled displacement parallel to the longitudinal axis of the plate but are substantially constrained against displacement perpendicular to the longitudinal axis of the plate. The bone screws with threaded heads may be rigidly fixed to the threaded receiving holes in the sliding elements without compressing the bone plate onto the bone surface. Sliding elements are elastically suspended inside the bone plate and undergo dynamic motion.

15 Claims, 11 Drawing Sheets

Related U.S. Application Data

(60) Provisional application No. 61/594,560, filed on Feb. 3, 2012.

(52) U.S. Cl.
CPC .......... *A61B 17/8052* (2013.01); *A61B 90/06* (2016.02); *A61B 17/8057* (2013.01); *A61B 2090/064* (2016.02); *A61B 2090/065* (2016.02); *A61B 2090/066* (2016.02)

(56) References Cited

U.S. PATENT DOCUMENTS

| | | |
|---|---|---|
| 3,807,394 A | 4/1974 | Attenborough |
| 4,029,091 A | 6/1977 | Von Bezold et al. |
| 4,338,296 A | 7/1982 | Lobmann et al. |
| 4,361,153 A | 11/1982 | Slocum et al. |
| 4,743,260 A | 5/1988 | Burton |
| 4,905,679 A | 3/1990 | Morgan |
| 4,943,292 A | 7/1990 | Foux |
| 5,306,310 A | 4/1994 | Siebels |
| 5,423,816 A | 6/1995 | Lin |
| 5,468,242 A | 11/1995 | Reisberg |
| 5,578,034 A | 11/1996 | Estes |
| 5,578,036 A | 11/1996 | Stone et al. |
| 5,681,311 A | 10/1997 | Foley et al. |
| 5,709,686 A | 1/1998 | Talos et al. |
| 5,741,258 A | 4/1998 | Klaue et al. |
| 5,743,913 A | 4/1998 | Wellisz |
| 5,984,925 A | 11/1999 | Apgar |
| 6,093,188 A | 7/2000 | Murray |
| 6,206,882 B1 | 3/2001 | Cohen |
| 6,340,632 B1 | 1/2002 | Fukada et al. |
| 6,364,881 B1 | 4/2002 | Apgar et al. |
| 6,540,746 B1 | 4/2003 | Buhler et al. |
| 6,663,632 B1 | 12/2003 | Frigg |
| 6,755,832 B2 | 6/2004 | Happomem et al. |
| 6,986,771 B2 | 1/2006 | Paul et al. |
| 6,989,011 B2 | 1/2006 | Paul et al. |
| 7,048,739 B2 | 5/2006 | Konieczynski et al. |
| 7,175,624 B2 | 2/2007 | Konieczynski et al. |
| 7,189,237 B2 | 3/2007 | Huebner |
| 7,276,070 B2 | 10/2007 | Mückter |
| 7,341,591 B2 | 3/2008 | Grinberg |
| 7,377,921 B2 | 5/2008 | Studer et al. |
| 7,452,370 B2 | 11/2008 | Anderson |
| 7,572,282 B2 | 8/2009 | Boomer et al. |
| 7,591,840 B2 | 9/2009 | Suddaby |
| D603,503 S | 11/2009 | Kriska et al. |
| D603,504 S | 11/2009 | Kriska et al. |
| D603,505 S | 11/2009 | Kriska et al. |
| D603,507 S | 11/2009 | Kriska et al. |
| D603,508 S | 11/2009 | Kriska et al. |
| D603,510 S | 11/2009 | Kriska et al. |
| D603,511 S | 11/2009 | Kriska et al. |
| D603,961 S | 11/2009 | Kriska et al. |
| D603,962 S | 11/2009 | Kriska et al. |
| D603,963 S | 11/2009 | Kriska et al. |
| D603,964 S | 11/2009 | Kriska et al. |
| 7,621,942 B2 | 11/2009 | Piehl |
| 7,641,675 B2 | 1/2010 | Lindemann et al. |
| 7,651,517 B2 | 1/2010 | Konieczynski et al. |
| 7,749,257 B2 | 7/2010 | Medoff |
| 7,806,914 B2 | 10/2010 | Boyd et al. |
| 7,811,312 B2 | 10/2010 | Stevens et al. |
| 7,833,256 B2 | 11/2010 | Biedermann et al. |
| 7,842,037 B2 | 11/2010 | Schulze |
| 7,887,569 B2 | 2/2011 | Frigg |
| 7,887,587 B2 | 2/2011 | Griffiths et al. |
| 7,914,561 B2 | 3/2011 | Konieczynski et al. |
| 8,486,070 B2 | 7/2013 | Morgan et al. |
| 8,687,865 B2 | 4/2014 | Wilson et al. |
| 8,790,379 B2 | 7/2014 | Bottlang et al. |
| 8,882,815 B2 | 11/2014 | Bottlang et al. |
| 8,992,583 B2 | 3/2015 | Bottlang et al. |
| 9,101,423 B2 | 8/2015 | Hulliger |
| 9,295,508 B2 | 3/2016 | Bottlang et al. |
| 9,510,879 B2 | 12/2016 | Bottlang et al. |
| 2002/0150671 A1 | 10/2002 | Koulik et al. |
| 2004/0006343 A1 | 1/2004 | Sevrain |
| 2004/0019353 A1 | 1/2004 | Freid et al. |
| 2004/0097937 A1 | 5/2004 | Pike et al. |
| 2004/0193155 A1 | 9/2004 | Castaneda |
| 2004/0220570 A1 | 11/2004 | Frigg |
| 2005/0090825 A1 | 4/2005 | Pfefferle et al. |
| 2005/0096657 A1 | 5/2005 | Autericque et al. |
| 2005/0116930 A1 | 6/2005 | Gates |
| 2005/0196421 A1 | 9/2005 | Hunter et al. |
| 2005/0216008 A1 | 9/2005 | Zwirnmann et al. |
| 2005/0273105 A1 | 12/2005 | Konieczynski et al. |
| 2005/0288668 A1 | 12/2005 | Brinkhaus |
| 2006/0058796 A1 | 3/2006 | Hartdegen et al. |
| 2006/0116682 A1 | 6/2006 | Longo |
| 2006/0155282 A1 | 7/2006 | Vese |
| 2006/0195099 A1 | 8/2006 | Bottlang |
| 2006/0241612 A1 | 10/2006 | Medoff |
| 2006/0247638 A1 | 11/2006 | Trieu et al. |
| 2006/0247639 A1 | 11/2006 | Anderson |
| 2006/0264949 A1 | 11/2006 | Kohut et al. |
| 2007/0055251 A1 | 3/2007 | Huebner et al. |
| 2007/0118127 A1 | 5/2007 | Serhan et al. |
| 2007/0213729 A1 | 9/2007 | Lindemann et al. |
| 2008/0027439 A1 | 1/2008 | Sasing |
| 2008/0083613 A1 | 4/2008 | Oi et al. |
| 2008/0147122 A1 | 6/2008 | Jackson |
| 2008/0147125 A1 | 6/2008 | Colleran et al. |
| 2008/0200955 A1 | 8/2008 | Tepic |
| 2008/0275509 A1 | 11/2008 | Clifford et al. |
| 2008/0306536 A1 | 12/2008 | Frigg et al. |
| 2009/0030467 A1 | 1/2009 | Sonohata et al. |
| 2009/0036930 A1 | 2/2009 | Allison |
| 2009/0043341 A1 | 2/2009 | Tyber et al. |
| 2009/0062915 A1 | 3/2009 | Kohm et al. |
| 2009/0118768 A1 | 5/2009 | Sixto, Jr. et al. |
| 2009/0118769 A1 | 5/2009 | Sixto, Jr. et al. |
| 2009/0118770 A1 | 5/2009 | Sixto, Jr. et al. |
| 2009/0125067 A1 | 5/2009 | Mazzuca et al. |
| 2009/0125069 A1 | 5/2009 | Sixto, Jr. et al. |
| 2009/0125070 A1 | 5/2009 | Sixto, Jr. et al. |
| 2009/0157121 A1 | 6/2009 | Harris et al. |
| 2009/0157123 A1 | 6/2009 | Appenzeller et al. |
| 2009/0222049 A1 | 9/2009 | Frigg et al. |
| 2009/0234393 A1 | 9/2009 | Sournac et al. |
| 2009/0270924 A1 | 10/2009 | Wing et al. |
| 2009/0318921 A1 | 12/2009 | White et al. |
| 2009/0318976 A1 | 12/2009 | Gabriel et al. |
| 2010/0010541 A1 | 1/2010 | Boomer et al. |
| 2010/0036430 A1 | 2/2010 | Hartdegen et al. |
| 2010/0076495 A1 | 3/2010 | Lindemann et al. |
| 2010/0094351 A1 | 4/2010 | Haggenmaker et al. |
| 2010/0114177 A1 | 5/2010 | Piehl |
| 2010/0131012 A1 | 5/2010 | Ralph et al. |
| 2010/0131013 A1 | 5/2010 | Ralph et al. |
| 2010/0217327 A1 | 8/2010 | Vancelette et al. |
| 2010/0249850 A1 | 9/2010 | Cerynik et al. |
| 2010/0305569 A1 | 12/2010 | Leuenberger et al. |
| 2011/0029024 A1 | 2/2011 | Crainich |
| 2011/0118742 A1 | 5/2011 | Hulliger et al. |
| 2011/0319942 A1 | 12/2011 | Bottlang et al. |
| 2012/0143193 A1 | 6/2012 | Hulliger |
| 2012/0277746 A1 | 11/2012 | Morgan et al. |
| 2012/0310289 A1 | 12/2012 | Bottland et al. |
| 2013/0006310 A1 | 1/2013 | Bottlang et al. |
| 2013/0204304 A1 | 8/2013 | Bottlang et al. |
| 2014/0330275 A1 | 11/2014 | Bottlang et al. |
| 2015/0025588 A1 | 1/2015 | Bottlang et al. |
| 2015/0230840 A1 | 8/2015 | Bottlang et al. |
| 2015/0327896 A1 | 11/2015 | Bottlang et al. |
| 2016/0074082 A1 | 3/2016 | Cremer et al. |

(56) References Cited

U.S. PATENT DOCUMENTS

2016/0081729 A1   3/2016   Velikov et al.
2016/0157905 A1   6/2016   Arellano et al.

FOREIGN PATENT DOCUMENTS

| EP | 1926445 A1 | 6/2008 |
|---|---|---|
| EP | 2005978 A1 | 12/2008 |
| FR | 742618 A | 1/1933 |
| FR | 2634368 A1 | 1/1990 |
| JP | 2009501575 A | 1/2009 |
| JP | 2010521274 A | 6/2010 |
| JP | 2015507953 A | 3/2015 |
| WO | WO-2005065557 A1 | 7/2005 |
| WO | WO-2007009124 A2 | 1/2007 |
| WO | WO-2009039430 A1 | 3/2009 |
| WO | WO-2010037984 A1 | 4/2010 |
| WO | WO-2010111350 A1 | 9/2010 |
| WO | WO-2010132252 A1 | 11/2010 |
| WO | WO-2011163387 A2 | 12/2011 |
| WO | WO-2013021357 A1 | 2/2013 |
| WO | WO2013116642 A1 | 8/2013 |
| WO | WO-2016014977 A1 | 1/2016 |

OTHER PUBLICATIONS

"U.S. Appl. No. 14/308,314, Non Final Office Action mailed Mar. 23, 2016", 9 pgs.
"Chinese Application Serial No. 201380011448.7, Office Action mailed Dec. 25, 2015", (W/ English Translation), 27 pgs.
"Standard specification for wrought titanium-6Aluminum-4Vanadium ELI (Extra Low Interstitial) alloy for surgical implant application. (UNS R56401)", ASTM F136-11, (2003), 5 pgs.
"Standard Test Methods for Equipment and Procedures Used in Evaluating the Performance Characteristics of Protective Headgear. Impact Test Apparatus.", ASMT F1446-13, (2013), 12 pgs.
Beaupre, G. S, et al., "A Comparison of Unicortical and Bicortical End Screw Attachment of Fracture Fixation Plates", Journal of Orthopaedic Trauma 6(3), (Feb. 1992), 294-300.
Davenport, Stephen R. et al., "Dynamic Compression Plate Fixation: A Biomechanical Comparison of Unicortical vs Bicortical Distal Screw Fixation", Journal of Orthopaedic Trauma 2(2), (Feb. 1988), 146-150.
Egol, Kenneth A, et al., "Biomechanics of Locked Plates and Screws". Journal of Orthopaedic Trauma 18(8), (Oct. 2004), 488-493.
Escott, Benjamin G. et al., "NeuFlex and Swanson Metacarpophalangeal Implants for Rheumatoid Arthritis: Prospective Randomized, Controlled Clinical Trial", The Journal of Hand Surgery 35(1), (Jan. 2010), 44-51.
Foliart, Donna E, "Synovitis and silicone joint implants: a summary of reported cases", Journal of Plastic and Reconstructive Surgery 99(1), (Jan. 1997), 245-252.
Gaggl. A. et al., "Biomechanical properties in titanium implants with integrated maintenance free shock absorbing elements", Journal of Biomaterials 22(2001), (Nov. 15, 2001), 3061-3066.
Gracis, S. E, et al., "Shock absorbing behavior of five restorative materials used on implants,", The International Journal of Prosthodontics 4(3), (Jan. 1992), 282-291.
U.S. Appl. No. 14/630,938, filed Feb. 25, 2015, Flexible Plate Fixation of Bone Fractures.
U.S. Appl. No. 13/755,493, filed Jan. 31, 2013, Bone Plate for Elastic Osteosynthesis.
U.S. Appl. No. 14/308,286, filed Jun. 18, 2014, Flexible Plate Fixation of Bone Fractures.
U.S. Appl. No. 14/308,314, filed Jun. 18, 2014, Flexible Plate Fixation of Bone Fractures.
U.S. Appl. No. 14/808,773, filed Jul. 24, 2015, Flexible Plate Fixation of Bone Fractures.
"U.S. Appl. No. 13/166,539, Final Office Action mailed May 21, 2014", 9 pgs.
"U.S. Appl. No. 13/166,539, Non Final Office Action mailed Jan. 2, 2014", 10 pgs.
"U.S. Appl. No. 13/166,539, Non Final Office Action mailed Jun. 28, 2013", 10 pgs.
"U.S. Appl. No. 13/166,539, Notice of Allowability mailed Oct. 9, 2014", 4 pgs.
"U.S. Appl. No. 13/166,539, Notice of Allowance mailed Aug. 15, 2014", 7 pgs.
"U.S. Appl. No. 13/166,539, Notice of Non-compliant Amendment mailed Feb. 20, 2014", 3 pgs.
"U.S. Appl. No. 13/166,539, Preliminary Amendment filed Jul. 19, 2012", 7 pgs.
"U.S. Appl. No. 13/166,539, Response filed Jan. 28, 2014 to Non Final Office Action mailed Jan. 2, 2014", 3 pgs.
"U.S. Appl. No. 13/166,539, Response filed May 2, 2014 to Non Final Office Action mailed Jan. 2, 2014", 14 pgs.
"U.S. Appl. No. 13/166,539, Response filed May 2, 2014 to Non Final Office Action mailed Feb. 20, 2014", 14 pgs.
"U.S. Appl. No. 13/166,539, Response filed May 6, 2013 to Restriction Requirement mailed Mar. 5, 2013", 9 pgs.
"U.S. Appl. No. 13/166,539, Response filed Jul. 21, 2014 to Final Office Action mailed May 21, 2014", 13 pgs.
"U.S. Appl. No. 13/166,539, Response filed Oct. 28, 2013 to Non Final Office Action mailed Jun. 28, 2013", 10 pgs.
"U.S. Appl. No. 13/166,539, Restriction Requirement mailed Mar. 5, 2013", 6 pgs.
"U.S. Appl. No. 13/490,249, Amendment filed Jan. 28, 2014", 3 pgs.
"U.S. Appl. No. 13/490,249, Non Final Office Action mailed Sep. 19, 2013", 10 pgs.
"U.S. Appl. No. 13/490,249, Notice of Allowance mailed Mar. 27, 2014", 7 pgs.
"U.S. Appl. No. 13/490,249, Response filed Jan. 21, 2014 to Non Final Office Action mailed Sep. 19, 2013", 12 pgs.
"U.S. Appl. No. 13/490,249, Response filed May 7, 2013 to Restriction Requirement mailed Mar. 7, 2013", 11 pgs.
"U.S. Appl. No. 13/490,249, Response filed Sep. 3, 2013 to Restriction Requirement mailed Jul. 2, 2013", 6 pgs.
"U.S. Appl. No. 13/490,249, Restriction Requirement mailed Mar. 7, 2013", 7 pgs.
"U.S. Appl. No. 13/490,249, Restriction Requirement mailed Jul. 7, 2013", 8 pgs.
"U.S. Appl. No. 13/554,119, Advisory Action mailed Feb. 12, 2014", 2 pgs.
"U.S. Appl. No. 13/554,119, Final Office Action mailed Sep. 19, 2013", 9 pgs.
"U.S. Appl. No. 13/554,119, Non Final Office Action mailed Mar. 13, 2013", 6 pgs.
"U.S. Appl. No. 13/554,119, Non Final Office Action mailed Jul. 16, 2014", 7 pgs.
"U.S. Appl. No. 13/554,119, Notice of Allowance mailed Nov. 24, 2014", 5 pgs.
"U.S. Appl. No. 13/554,119, Preliminary Amendment filed Jun. 20, 2012", 5 pgs.
"U.S. Appl. No. 13/554,119, Response filed Jan. 28, 2014 to Final Office Action mailed Sep. 19, 2013", 3 pgs.
"U.S. Appl. No. 13/554,119, Response filed Mar. 19, 2014 to Advisory Action mailed Feb. 12, 2014", 13 pgs.
"U.S. Appl. No. 13/554,119, Response filed Aug. 13, 2013 to Non Final Office Action mailed Mar. 13, 2013", 8 pgs.
"U.S. Appl. No. 13/554,119, Response filed Oct. 16, 2014 to Non Final Office Action mailed Jul. 16, 2014", 12 pgs.
"U.S. Appl. No. 13/755,493, Advisory Action mailed Dec. 4, 2015", 4 pgs.
"U.S. Appl. No. 13/755,493, Examiner Interview Summary mailed Dec. 4, 2015", 1 pg.
"U.S. Appl. No. 13/755,493, Final Office Action mailed Jul. 9, 2015", 12 pgs.
"U.S. Appl. No. 13/755,493, Non Final Office Action mailed Nov. 19, 2014", 13 pgs.
"U.S. Appl. No. 13/755,493, Notice of Allowance mailed Dec. 23, 2015", 5 pgs.
"U.S. Appl. No. 13/755,493, Preliminary Amendment mailed Jan. 28, 2014", 3 pgs.

(56) References Cited

OTHER PUBLICATIONS

"U.S. Appl. No. 13/755,493, Response filed Feb. 19, 2015 to Non-Final Office Action mailed Nov. 19, 2014", 16 pgs.
"U.S. Appl. No. 13/755,493, Response filed Oct. 28, 2014 to Restriction Requirement mailed Oct. 9, 2014", 9 pgs.
"U.S. Appl. No. 13/755,493, Response filed Nov. 12, 2015 to Final Office Action mailed Jul. 9, 2015", 15 pgs.
"U.S. Appl. No. 13/755,493, Response filed Dec. 9, 2015 to Advisory Action mailed Dec. 4, 2015", 12 pgs.
"U.S. Appl. No. 13/755,493, Restriction Requirement mailed Oct. 9, 2014", 6 pgs.
"U.S. Appl. No. 13/755,493, Supplemental Preliminary Amendment mailed Jan. 30, 2014", 3 pgs.
"U.S. Appl. No. 14/308,286, Preliminary Amendment filed Sep. 17, 2014", 7 pgs.
"U.S. Appl. No. 14/308,314, Preliminary Amendment filed Sep. 17, 2014", 7 pgs.
"U.S. Appl. No. 14/630,938, Preliminary Amendment filed Oct. 19, 2015", 7 pgs.
"Australian Application Serial No. 2011270934, First Examiner Report mailed Sep. 12, 2013", 4 pgs.
"Australian Application Serial No. 2011270934, Response filed Jun. 30, 2014 to First Examiner Report mailed Sep. 12, 2013", 20 pgs.
"Australian Application serial No. 2014265031, Non Final Office Action mailed Sep. 21, 2015", 3 pgs.
"Australian Application Serial No. 2014265031, Preliminary Amendment filed Jul. 28, 2015", 13 pgs.
"European Application Serial No. 11798862.6, Extended European Search Report mailed Mar. 16, 2015", 12 pgs.
"European Application Serial No. 11798862.6, Office Action mailed Feb. 1, 2013", 2 pgs.
"European Application Serial No. 11798862.6, Response filed Jul. 30, 2013 to Office Action mailed Feb. 1, 2013", 8 pgs.
"European Application Serial No. 13743819.8, Extended European Search Report mailed Nov. 11, 2015", 9 pgs.
"European Application Serial No. 13743819.8, Preliminary Amendment filed Mar. 26, 2015", 11 pgs.
"International Application Serial No. PCT/US2011/041484, International Preliminary Report on Patentability mailed Jan. 10, 2013", 6 pgs.
"International Application Serial No. PCT/US2011/041484, International Search Report mailed Feb. 17, 2012", 4 pgs.
"International Application Serial No. PCT/US2011/041484, Written Opinion mailed Feb. 17, 2012", 4 pgs.
"International Application Serial No. PCT/US2013/024336, International Preliminary Report on Patentability mailed Aug. 14, 2014", 10 pgs.
"International Application Serial No. PCT/US2013/024336, International Search Report mailed May 15, 2013", 4 pgs.
"International Application Serial No. PCT/US2013/024336, Written Opinion mailed May 15, 2013", 8 pgs.
"International Application Serial No. PCT/US2015/042057, International Search Report mailed Oct. 16, 2015", 4 pgs.
"International Application Serial No. PCT/US2015/042057, Written Opinion mailed Oct. 16, 2015", 6 pgs.
Bottlang, et al., "A Nonlocking End Screw Can Decrease Fracture Risk Caused by Locked Plating in the Osteoporotic Diaphysis", Journal of Bone & Joint Surgery, vol. 91, (2009), 620-627 pgs.
Bottlang, et al., "Effects of Construct Stiffness on Healing of Fractures Stabilzed with Locking Plates", Journal of Bone & Joint Surgery, vol. 92, (2010), 12-22 pgs.
Fitzpatrick, Dan C. et al., "Relative Stability of Conventional and Locked Plating Fixation in a Model of the Osteoporotic Femoral Diaphysis", Journal of Clinical Biomechanics 24(2), (Feb. 2009), 203-209.
Gard, S. A. et al., "The effect of a shock-absorbing pylon on the gait of persons with unilateral transtibial amputation.", Journal of Rehabilitation Research and Development 40(2), (2003), 109-124.
"U.S. Appl. No. 14/308,286, Corrected Notice of Allowance mailed Jun. 28, 2016", 4 pgs.
"U.S. Appl. No. 14/308,286, Notice of Allowance mailed Aug. 5, 2016", 7 pgs.
"U.S. Appl. No. 14/308,314, Final Office Action mailed Aug. 28, 2016", 8 pgs.
"U.S. Appl. No. 14/308,314, Response filed Jul. 25, 2016 to Non Final Office Action mailed Mar. 23, 2016", 11 pgs.
"U.S. Appl. No. 14/308,314, Response filed Nov. 23, 2016 to Final Office Action mailed Aug. 23, 2016", 10 pgs.
"U.S. Appl. No. 14/630,938, Final Office Action mailed Dec. 20, 2016", 5 pgs.
"U.S. Appl. No. 14/630,938, Non Final Office Action mailed Aug. 9, 2016", 14 pgs.
"U.S. Appl. No. 14/630,938, Response filed Nov. 9, 2016 to Non Final Office Action mailed Aug. 9, 2016", 16 pgs.
"Australian Application Serial No. 2013214894, First Examiner Report mailed Oct. 6, 2016", 3 pgs.
"Australian Application Serial No. 2016203422, First Examiners Report mailed Oct. 19, 2016", 4 pgs.
"Chinese Application Serial No. 201380011448.7, Office Action mailed Oct. 27, 2016", (W/ English Translation), 19 pgs.
"Chinese Application Serial No. 201380011448.7, Response filed Jul. 8, 2016 to Office Action mailed Dec. 25, 2015", 7 pgs.
"Japanese Application Serial No. 2014-555748, Office Action mailed Nov. 15, 2016", (W/ English Translation), 6 pgs.
Rockwood, Charles A, et al., Rockwood and Green's fractures in adults, Lippincott Company, (Jan. 1, 1991), 16 pgs.
"U.S. Appl. No. 14/308,314, Non Final Office Action mailed Feb. 7, 2017", 9 pgs.
"U.S. Appl. No. 14/630,938, Notice of Allowance mailed Mar. 27, 2017", 5 pgs.
"U.S. Appl. No. 14/630,938, Response filed Feb. 28, 2017 to Final Office Action mailed Dec. 20, 2016", 11 pgs.
"U.S. Appl. No. 14/808,773, Preliminary Amendment Filed Feb. 9, 2017", 3 pgs.
"Australian Application Serial No. 2013214894, Amendment filed Mar. 8, 2017", 2 pgs.
"Australian Application Serial No. 2013214894, Response Filed Mar. 3, 2017 to Office Action Mailed Oct. 6, 2017", 17 pgs.
"Australian Application Serial No. 2016203422, Response Filed Mar. 2, 2017 to Office Action mailed Oct. 19, 2016", 9 pgs.
"Canadian Application Serial No. 2,803,585, Office Action mailed Jan. 25, 2017", 4 pgs.
"Chinese Application Serial No. 201380011448.7, Response filed Jan. 11, 2017 to Office Action mailed Oct. 27, 2016", (With English translation of claims), 10 pgs.
"International Application Serial No. PCT/US2015/042057, International Preliminary Report on Patentability mailed Feb. 9, 2017", 8 pgs.
"Japanese Application Serial No. 2014-555748, Response Filed Feb. 15, 2017 to Office Action mailed Nov. 15, 2016", (W/ English Translation), 14 pgs.

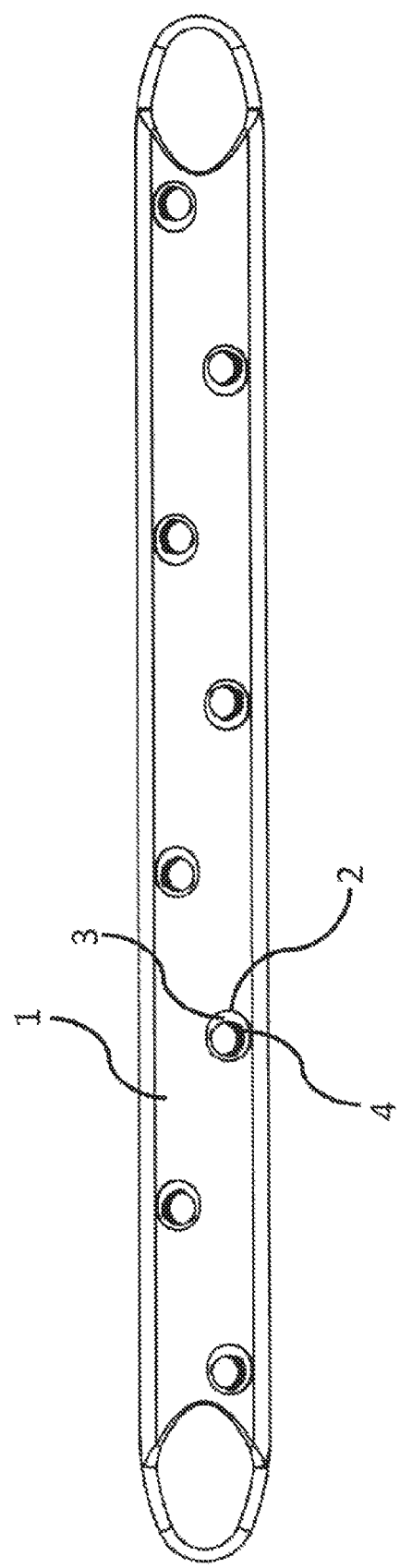

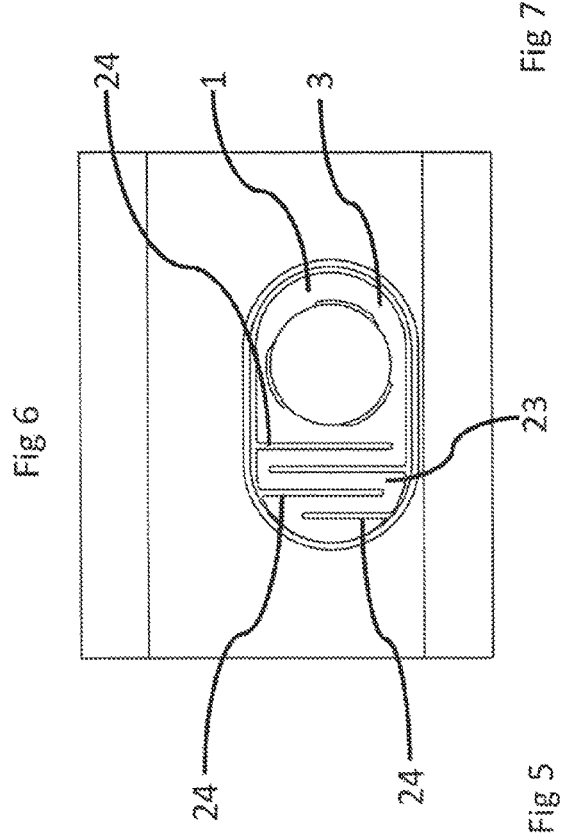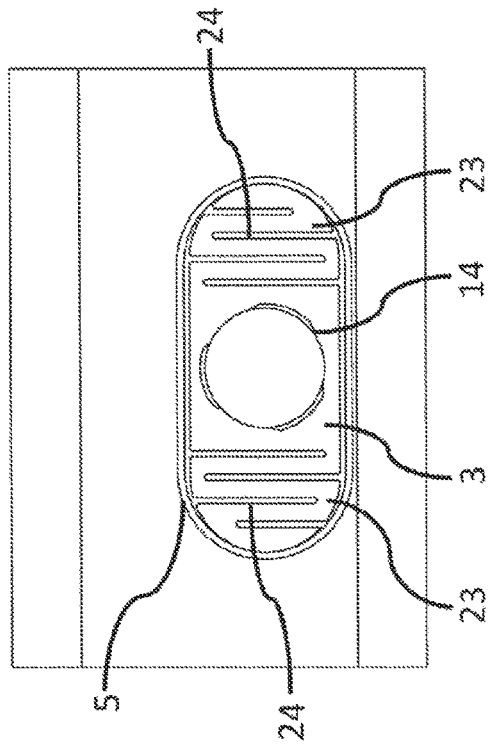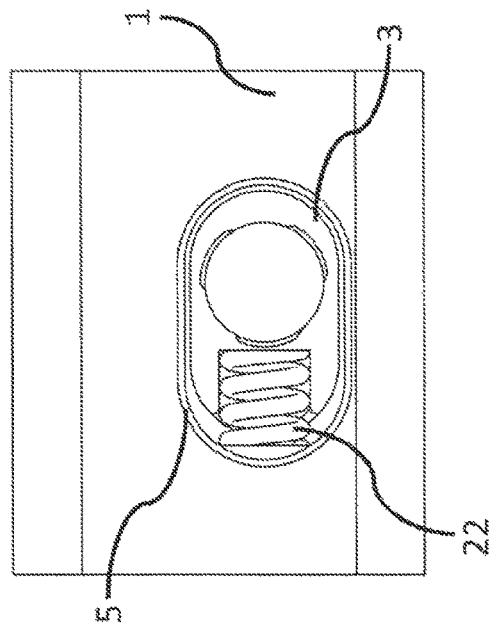

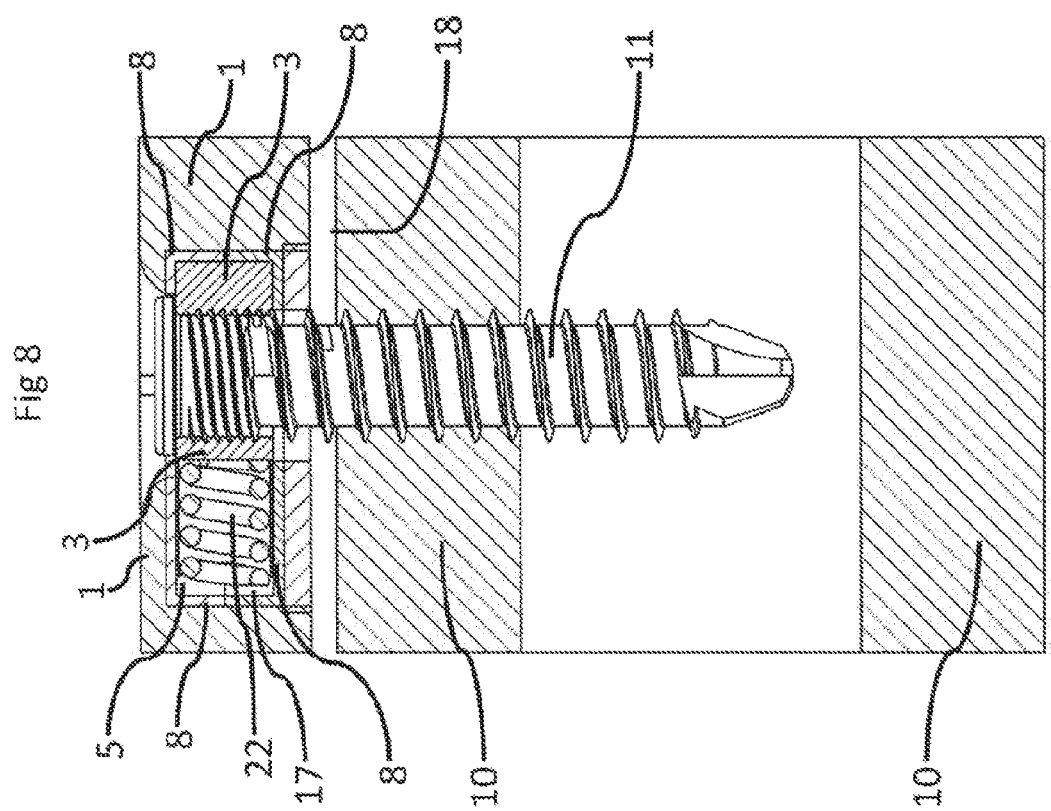

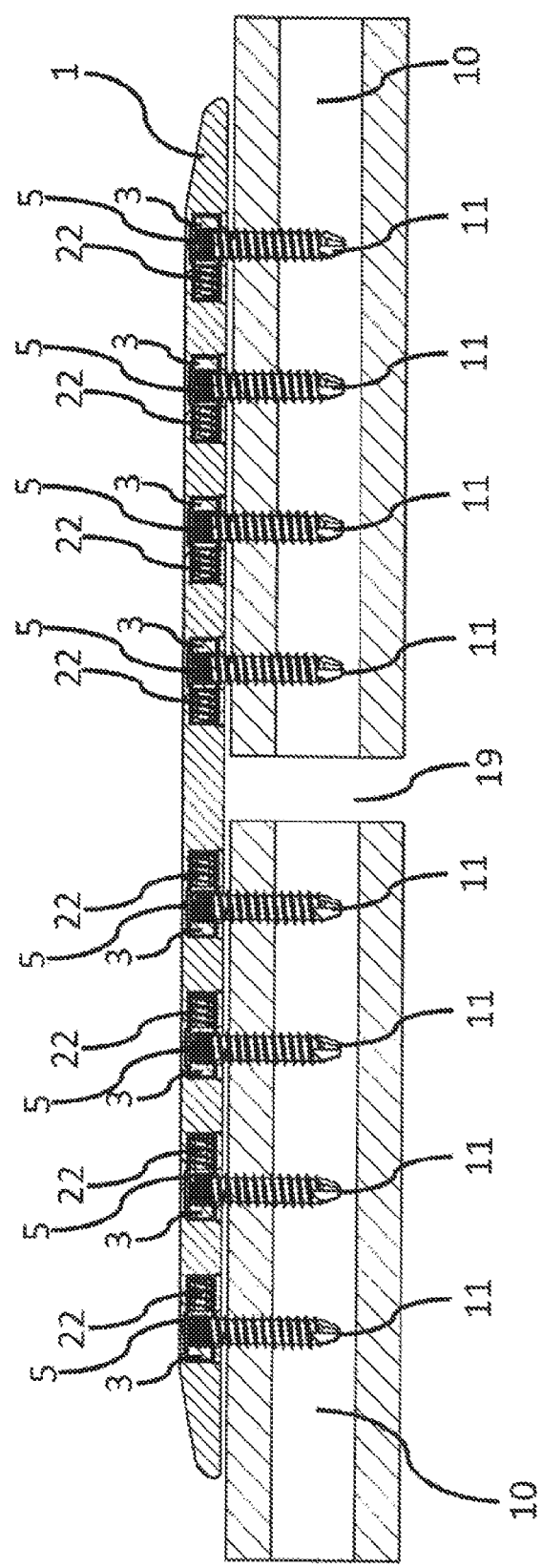

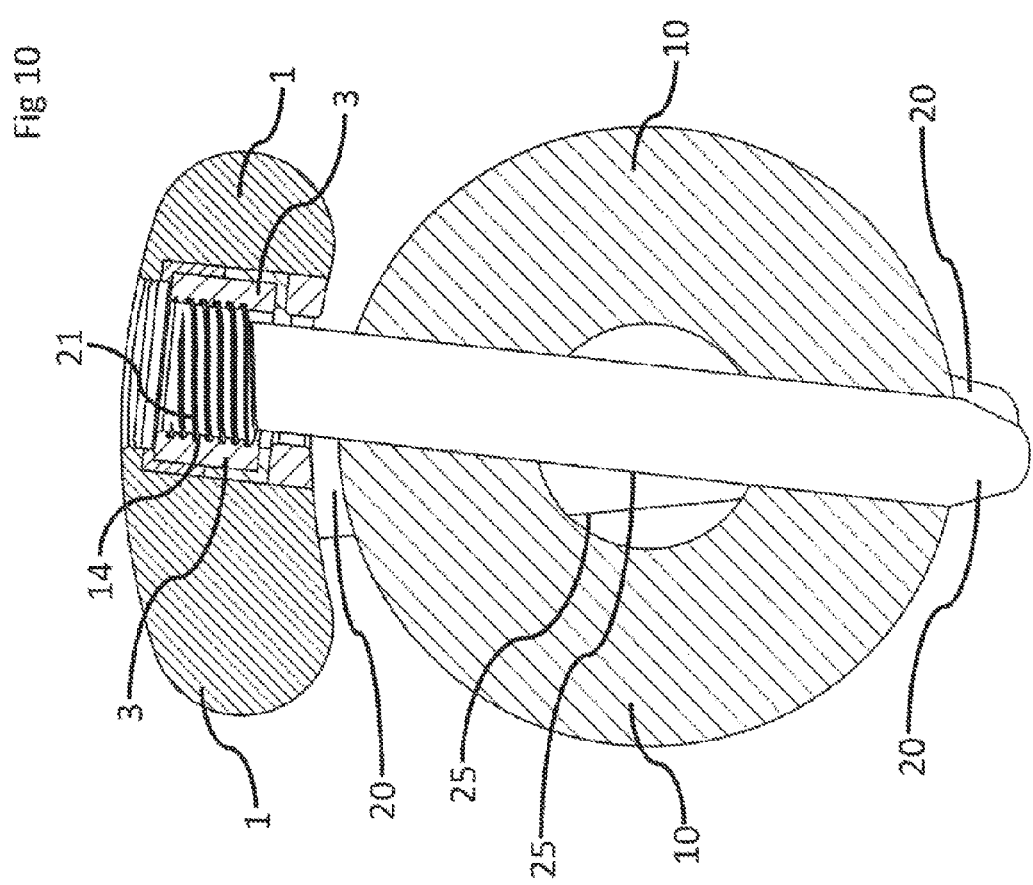

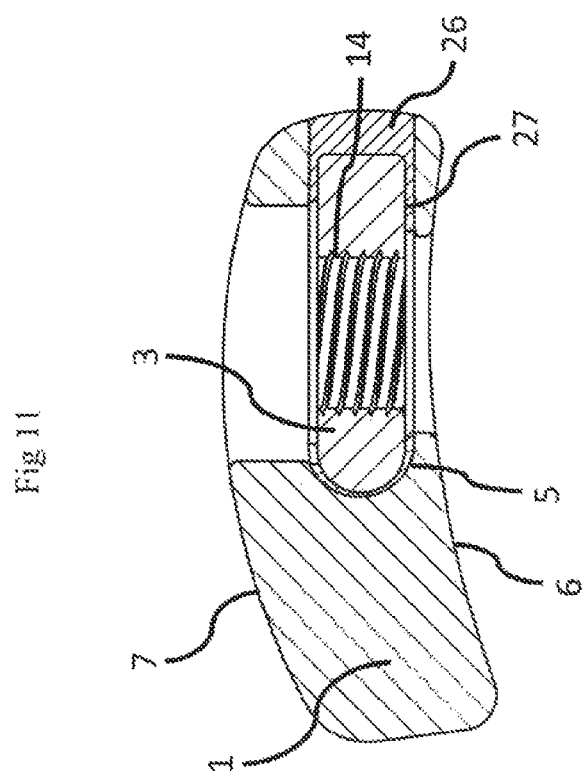

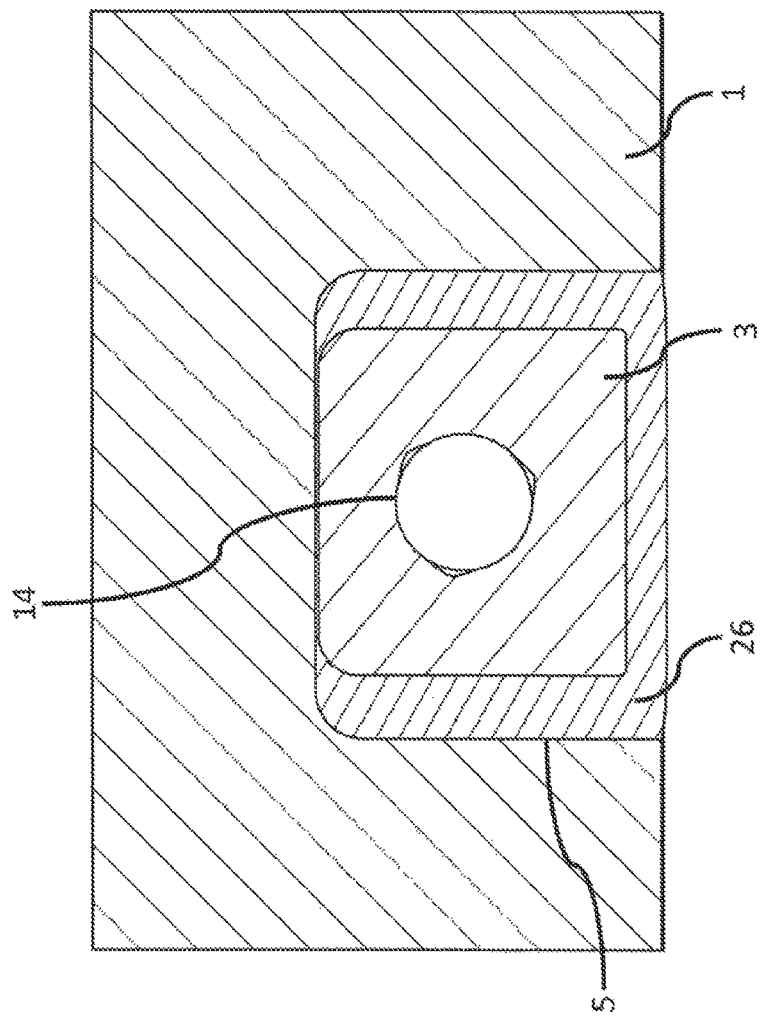

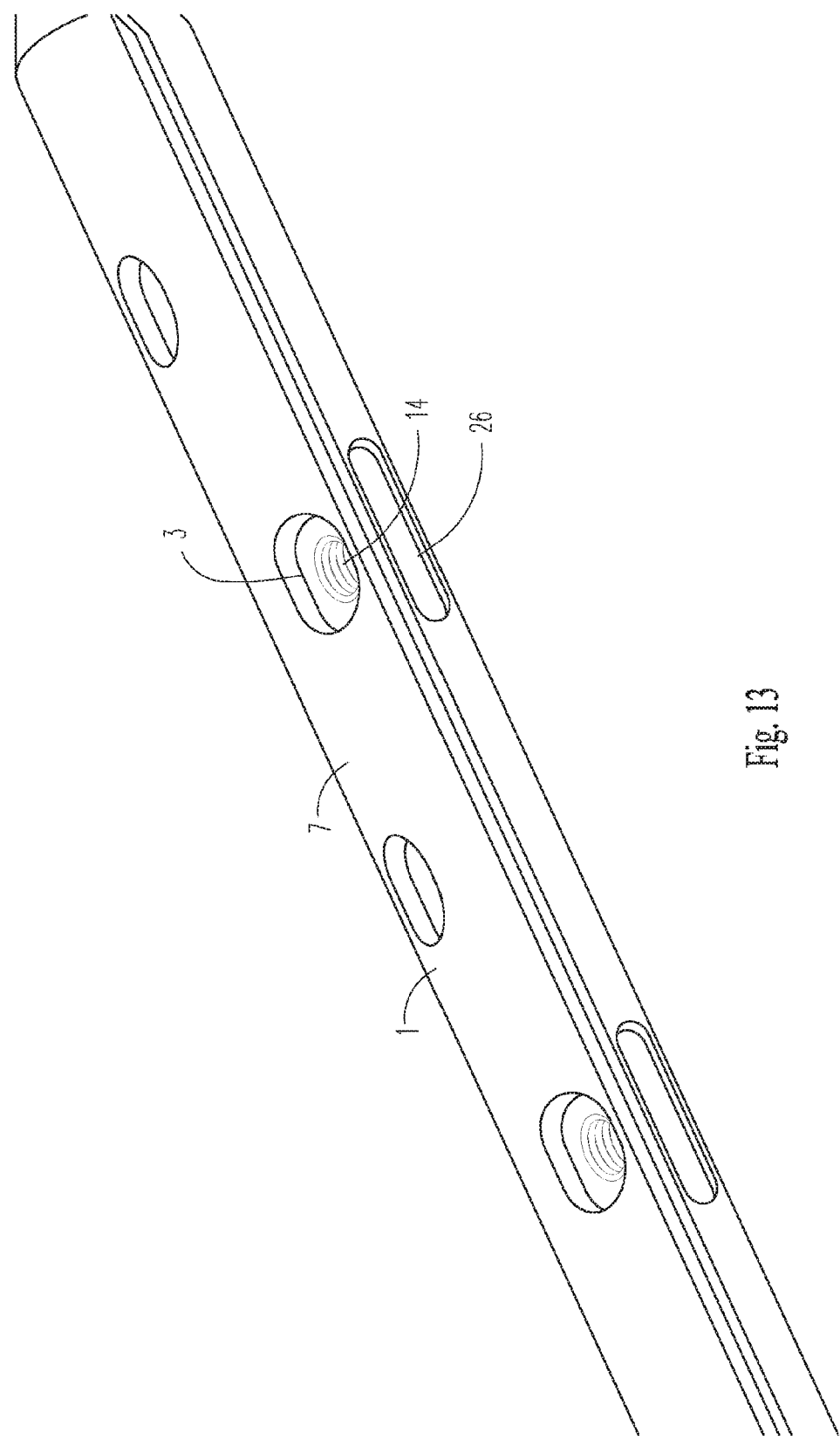

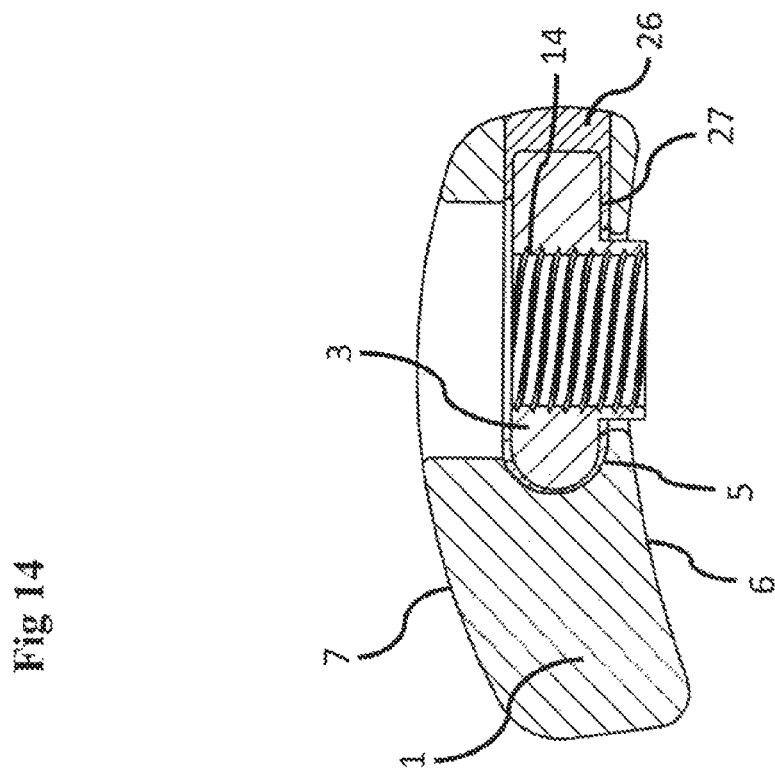

BONE PLATE FOR ELASTIC OSTEOSYNTHESIS

RELATED APPLICATIONS

This application claims priority to U.S. provisional application 61/594,560, filed on Feb. 3, 2012, which is herein incorporated by reference in its entirety.

GOVERNMENT INTEREST

This invention was made with government support under AR061201 awarded by the National Institutes of Health. The government has certain rights in this invention.

TECHNICAL FIELD

Embodiments herein relate generally to devices for fixation of a fractured bone. Specifically, the disclosure relates to a bone plate that provides elastic fixation of a fracture. Such elastic fixation enables small motion at the fracture site to promote natural fracture healing by formation of a fracture callus.

BACKGROUND

Osteosynthesis plates for stabilization of bone fractures typically are applied with bone screws. Traditionally, bone screws compress a plate onto the bone surface to provide stable fixation. More recently, locking plates have been introduced, which typically have threaded receiving holes for positive, angle-stable fixation of locking screws that have a correspondingly threaded screw head. These locked plating constructs can provide more durable fixation than traditional non-locked constructs, particularly in weak osteoporotic bone, However, the inherent stiffness of locked plating constructs causes two clinical challenges. First, it may alter the load distribution in bone, which may either cause bone resorption in load-shielded regions adjacent to the plate, or bone fracture due to implant-induced stress risers. Second, the high stiffness of an osteosynthesis plate construct suppresses relative displacement between bone fragments; however, such interfragmentary motion is important to promote the natural cascade of fracture healing by callus formation. Therefore, overly stiff locking plate constructs may delay or prevent fracture healing, which may also lead to implant breakage or loss of screw fixation in the bone.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 1 is a top view of a bone plate in accordance with various embodiments.

FIG. 5 is a bottom view of a sliding element and a spring element inside a bone plate shown without a bottom to visualize the sliding element, in accordance with various embodiments.

FIG. 6 is a bottom view of a sliding element and integrated spring element inside the bone plate shown without a bottom to visualize the sliding element, in accordance with various embodiments.

FIG. 7 is a bottom view of a sliding element and integrated spring elements inside the bone plate shown without a bottom to visualize the sliding element in accordance with various embodiments.

FIG. 8 is a sectional view of a sliding element shown in association with a bone screw affixed to a cylindrical bone segment, in accordance with various embodiments.

FIG. 9 is a sectional view of a bone plate shown in association with bone screws affixed to two corresponding segments of a cylindrical bone, in accordance with various embodiments.

FIG. 10 is a cross-sectional view of a bone plate affixed with non-collinear locking pegs to a cylindrical bone segment, in accordance with various embodiments.

FIG. 11 is a transverse cross-sectional view of a bone plate and sliding element with cylindrical threading and an elastomer lumen suspending said sliding element inside the bone plate, in accordance with various embodiments.

FIG. 12 is a bottom view of a sliding element and elastomer lumen within a slot in the side of the bone plate shown without a bottom to visualize the sliding element in accordance with various embodiments.

FIG. 13 shows a top view of a bone plate in accordance with various embodiments.

FIG. 14 shows a transverse cross-sectional view a sliding element with cylindrical threading, in accordance with various embodiments.

DETAILED DESCRIPTION

Figure 4:
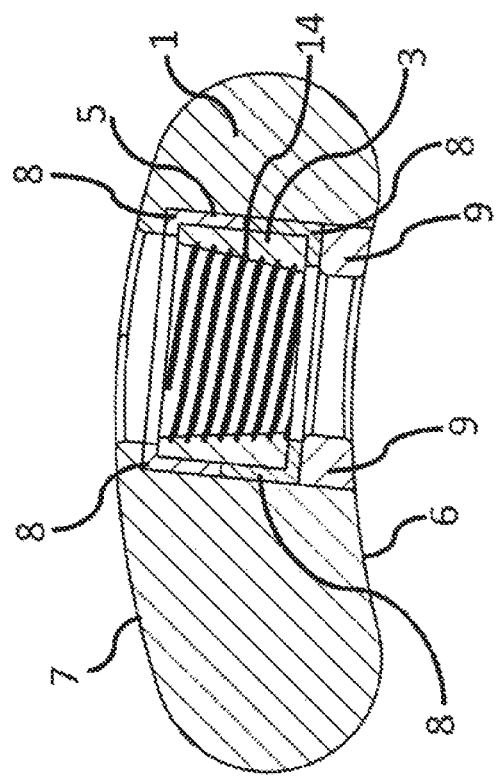
FIG. 4 is a transverse cross-sectional view of a sliding element with conical threading, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

In various embodiments, methods, apparatuses, and systems for elastic fixation of a fracture are provided.

Embodiments herein provide an osteosynthesis plate that allows for stable fixation of a bone fracture, while permitting elastic dynamic motion along the longitudinal axis of the bone plate while maintaining stability in all other directions at the fracture site to stimulate fracture healing by callus formation.

FIG. 1 illustrates a top view of an oblong bone plate with elongated plate holes 2 that are arranged generally along the longitudinal plate axis in a staggered pattern. Sliding elements 3 reside below the surface of bone plate 1 in a manner that the threaded through-hole 4 of the sliding element coincides with the elongated plate hole 2 of bone plate 1. Sliding elements 3 have threaded through-holes 4 for engagement of correspondingly threaded bone fasteners. The through-holes 4 may be oriented substantially perpendicular to the upper surface of bone plate 1. The through-holes 4 may also be angled toward the longitudinal midline of the plate so that a bone fastener inserted into a staggered/offset screw hole will be directed/angled toward the midsection of a bone member to which the plate is coupled. See FIGS. 3 and 10.

Figure 2:
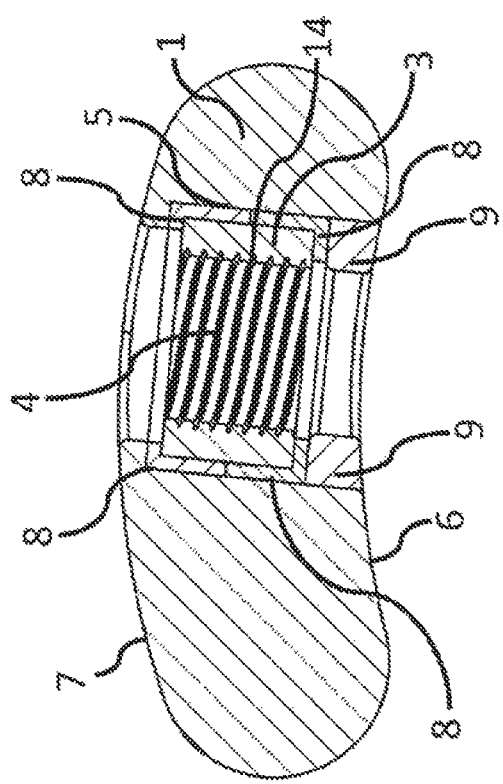
FIG. 2 is a transverse cross-sectional view a sliding element with cylindrical threading, in accordance with various embodiments.

FIG. 2 illustrates a transverse cross-section through the bone plate 1 and through the threaded through-hole 4 of sliding element 3. The through-hole 4 is oriented generally perpendicular to the convex upper surface of bone plate 1. The sliding element 3 is generally bar-shaped and of rectangular cross-section. In other embodiments, other cross-sectional shapes may be used, such as square, oval, curved, or a curved rectangle that approximates the cross-sectional shape of the plate. The sliding element is comprised of any medically acceptable material, such as but not limited to a metal like titanium or stainless steel. Sliding element 3 is located in a correspondingly shaped recess 5 that extends to the bottom plate surface 6 and that extends toward the upper plate surface 7 without penetrating through upper plate surface 7 in order to preserve the bending strength of the plate. As shown in FIG. 2, the recess for the sliding element extends through to the bottom plate to the bottom surface, and the sliding element is subsequently retained in the plate with a bottom cover 9. Recess 5 is lined with a low-friction member 8 to reduce friction and wear between the sliding element 3 and recess 5. The low friction member is any medically acceptable material, such as, but not limited to a polymer, such as PEEK (Polyether ether ketone). Other exemplary biocompatible polymers with a low coefficient of friction may be used, such as UHMWPE (Ultrahigh molecular weight polyethylene). Alternatively, the space between the sliding element and the recess may be filled with a silicone derivative that provides a hyper-elastic interface, which may serve to reduce friction and/or to provide an elastic suspension of the sliding element in the recess.

Sliding element 3 is retained inside plate 1 by a bottom cover 9, which is rigidly connected by laser welding, press-fit, or comparably reliable bonding means to plate 1 after insertion of the sliding element. Therefore, sliding element 3 is constrained within bone plate 1 to prevent slider motion perpendicular to the longitudinal axis of bone plate 1. The sliding element 3 may be coupled to a bone member 10 with a locking bone screw 11, which may be a screw that has a threaded screw shaft 12 and a threaded screw head 13 (See FIG. 3)). One preferred locking screw has the same thread outer diameter and thread pitch at the screw head 13 and screw shaft 12. While screw head 13 and screw shaft 12 have the same pitch, i.e. slope of the revolving helix, screw shaft 12 has a single helix and screw head 13 has three helices that simultaneously revolve around the core diameter. This arrangement allows for a larger core diameter in screw head 13 compared to screw shaft 12, making the thread appear denser. This arrangement also has the advantage that the screw shaft is engaged in the threaded hole 14 of sliding element 3 throughout screw insertion. It therefore provides a means to rigidly connect sliding element 3 to bone member 10 at a given elevation over the bone surface without having to compress the sliding element or bone plate against the bone surface. It furthermore prevents screw head 13 from being compressed against sliding element 3 rather than engage into sliding element 3. Positive locking of the bone screw in sliding element 3 is provided by end cap 15 of the screw head 13, which is compressed against the upper surface of sliding element 3.

FIG. 4 illustrates an alternative embodiment of through-hole 14, wherein the threaded hole 14 in the sliding element is conical. This will enable positive locking of a correspondingly threaded conical screw head in the sliding element 3.

FIG. 5 illustrates a bottom view of bone plate 1 without bottom cover 9 to visualize sliding element 3. The longitudinal dimension of the sliding element 3 is less than the corresponding longitudinal dimension of recess 5. This difference in longitudinal dimension determines the permissible axial motion of sliding element 3 relative to plate 1. This controlled range of axial motion ranges from 0.2-2 mm, preferably from 0.3-1 mm. A spring element, such as spring 22, forces sliding element 3 into a defined resting positing by application of an effective spring pre-load in the range of 1-100 N, preferably 5-50 N. If the sliding element 3 is exerting a force against the pre-load of spring element 22, motion of the sliding element relative to the plate is initiated (linear motion along the longitudinal axis of the bone plate). Upon removal of the force, sliding element 3 returns to its resting position by the spring force. One example of pre-loading a spring element is as follows. To preload the spring element, during assembly the spring element is compressed before or when the sliding element and/or spring element is inserted into the bone plate.

FIG. 6 illustrates an alternative embodiment of a spring element, in which a spring element is integrated into, or is part of the sliding element 3 (as opposed to a separate spring) by means of a series of elongate spring fingers 23 and channels 24. Channels 24 transform a portion of the sliding element 3 into an elastic spring element.

FIG. 7 illustrates yet another alternative embodiment of a spring element, in which channels 24 are introduced at opposite sides of sliding element 3. Channels 24 transform opposing sides of sliding element 3 into elastic spring elements, which elastically suspend the threaded screw hole 14 inside recess 5, and which allow bi-directional translation of the threaded through-hole 14 from its unloaded center position.

FIG. 8 illustrates a longitudinal cross-sectional view of an embodiment of sliding element 3 shown in association with a bone screw 11 affixed to a cylindrical bone segment 10. Spring 22 is recessed in a cylindrical hole 17 in sliding element 3. Recess 5 is lined with a low-friction layer 8. Locking screw 11 fixes sliding element 3 in a manner that plate 1 is not compressed onto the bone surface 18. In an alternative embodiment using non-locking screws, the plate may be compressed on the bone surface.

FIG. 9 illustrates a cross-sectional view of bone plate 1 that is elastically fixed to two corresponding segments of a cylindrical bone 10 with bone screws 11. Springs 22 in sliding elements 3 are located toward the fracture site 19. Application of external compressive force acting upon bone segments 10 will therefore induce translation/movement of sliding elements 3 relative to plate 1, which in turn will induce translation of the bone segments 10 parallel to the longitudinal axis of plate 1. This will generate symmetric motion between the surfaces at fracture site 19 within a controlled motion envelope. The amount of fracture site motion is controlled by the maximal extent of slider translation inside recess 5 of plate 1. Hence, based on the stiffness and pre-load of the spring elements, external compressive force in excess of a predetermined threshold of between 100-1000 N, preferably 200-800 N will not yield additional motion of sliding elements 3 inside the plate. If the pre-load and stiffness of the spring elements are selected to be sufficiently small, the sliding elements will reach their maximal permissible displacement at an external compressive force that is sufficiently low to prevent excessive plate bending, which otherwise could lead to excessive friction, wear, or jamming of sliding members 3 inside their recess.

Elastic coupling of a bone plate to a bone by means of elastically suspended sliding elements may be applied to one or more bone segments of a fractured bone, while other bone segments may be fixed to the same bone plate using standard bone fasteners, such as non-locking or locking screws.

FIG. 10 illustrates a cross-section of bone plate 1 in association with a cylindrical bone 10, wherein plate 1 is affixed to bone 10 with multiple non-collinear bone pegs 20. Bone pegs 20 have a threaded head 21 and are positively locked into the correspondingly threaded through-hole 14 of sliding element 3. Bone pegs 20 have a smooth shaft 25 for multi-planar fixation in the bone, wherein the smooth shaft prevents transmission of forces acting in direction of the peg longitudinal axis onto the sliding element 3.

FIG. 11 illustrates a transverse cross-section of bone plate 1 through the threaded through-hole 14 of sliding element 3. The sliding element 3 is at least partially enclosed in recess 5. In certain embodiments, the sliding element is enclosed at the top, bottom, and towards the plate center, but in certain embodiment is actually exposed on the side. By leaving it open on one side, the sliding element can be dropped into place and the silicone can be molded and thus, one would not have to weld a plate over it. In this embodiment, recess 5 is created through the side of bone plate 1 and extends through to the bottom plate surface 6 and that extends toward the upper plate surface 7. Sliding element 3 is suspended within recess 5 by an elastomer lumen 26. The elastomer lumen 26 may be selectively bonded to portions of recess 5 and/or sliding element 3 to affect a desired elastic constraint of the sliding element 3 relative to bone plate 1. For example, in one embodiment, the surface 27 of the sliding element 3 is bonded to the elastomer lumen or elastic material. FIG. 11 shows the situation where the sliding element is restrained against motion. In addition to preventing metal-on-metal contract and abrasive wear, this elastic confinement of the sliding element facilitates engagement of threaded screw heads into the sliding element, especially in the case where a screw is inserted not exactly parallel to the axis of the screw hole in the sliding element.

FIG. 12 illustrates a bottom view of bone plate 1 without the bottom to visualize sliding element 3 with threaded through-hole 14. Sliding element 3 is enclosed in recess 5 created in the side of bone plate 1 by an elastomer lumen 26 that preferentially allows for longitudinal motion. This figure shows an embodiment where the longitudinal dimension of the sliding element 3 is less than the corresponding longitudinal dimension of recess 5. This difference in longitudinal dimension determines the permissible motion of sliding element 3 relative to plate 1. This controlled range of motion ranges from 0.1-2 mm, preferably from 0.3-1 mm. In the embodiment shown, sliding element 3 does not extend to the outside surface of bone plate 1. FIG. 12 shows the elastomer 26 between the edges of the sliding element 3 and the recess area 5. In other embodiments, the elastomer is an elastomer lumen 26 that surrounds or encases the sliding element 3.

FIG. 13 illustrates a three dimensional view of the bone plate 1 with a top surface 7 and a sliding element 3 with a threaded through-hole 14. This figure shows a recess on the "side of the bone plate" (i.e. not the top surface or the bone facing surface) through which the sliding element 3 and elastomer lumen 26 can be inserted.

FIG. 14 shows the sliding element 3 protruding down past the bottom surface 6 of the bone plate 1. The sliding element 3 with a threaded through hole 14 resides in the recess 5. The elastomer lumen 26 is shown surrounding the sliding element 3. This figure shows the internal sliding element 3 is at least partially enclosed within a cavity in the side of the bone plate (i.e. a cavity that is not the bone facing or top facing surface). This figure is designed to show a part of the slider that extends below the bottom surface. The cavity is still in the side of the plate. The surface 27 of the sliding element 3 is bonded to the elastomer lumen or elastic material.

In an embodiment, there is provided a bone plate having an outer surface and a bone-facing surface, the bone plate comprising internal sliding elements, wherein each sliding element contains a threaded receiving hole for bone screws or pegs that have a correspondingly threaded screw head. The sliding elements undergo controlled displacement parallel to the longitudinal axis of the plate but are substantially constrained against displacement perpendicular to the longitudinal axis of the plate. The bone screws with threaded heads can be rigidly fixed to the threaded receiving holes in the sliding elements without compressing the bone plate onto the bone surface. Therefore, a bone segment can be securely fixed to the bone plate, while retaining the ability for controlled displacement parallel to the long axis of the bone plate. The amount of displacement is controlled by the motion envelope of the sliding elements within the bone plate.

The sliding element is generally bar-shaped and of rectangular cross-section. In other embodiments, other cross-sectional shapes may be used, such as square, oval, curved, or a curved rectangle that approximates the cross-sectional shape of the plate. The sliding element just needs to be sized and shaped to fit into the recess of the plate and sized to allow the desired amount of motion. The sliding element is comprised of any medically acceptable material, such as but not limited to a metal like titanium or stainless steel.

The sliding elements may be elastically suspended in the plate by means of a spring element that determines the amount of translation of the sliding element relative to the plate in response to a load acting in a longitudinal direction of the plate. This elastic suspension enables dynamic motion between adjacent bone segments affixed to the bone plate in response to weight bearing of the plate-bone fixation construct. The spring element may be a spring that is separate from the sliding element or the spring element may be part of the sliding element. In other embodiments the spring element is an elastomeric material.

Elastic fixation of the bone to the plate through load-responsive sliding elements enables controlled and symmetric motion at the fracture site, which is known to promote fracture healing by callus formation. Furthermore, elastic fixation enhances load distribution between fixation points, which reduces stress concentrations and thereby enhances construct strength. Elastic fixation furthermore reduces bone resorption and porosis caused by stress-shielding due to overly rigid fixation constructs.

Elastic fixation may be through the use of an elastomer. The elastomer may positively adhere at least to a portion of the plate or the sliding element surface to affect a desired elastic constraint of the sliding element relative to the bone plate.

In certain embodiments, the elastomer is free of voids (e.g. air pockets) or is substantially free of voids. In other embodiments the elastomer has voids which can further reduce the effective stiffness of the system by increasing the compressibility of the elastomer.

The elastomer can be any medically suitable elastomer, such as, but not limited to silicone. In certain embodiments, the elastomer has a modulus of elasticity in the range of 0.1-50 MPa, which allows for the desired amount of movement/elasticity. In certain embodiments the elastic modulus and formulation of the elastomer material may differ within the elastomer, for example, which might be the case if two different elastomers are used or if different thicknesses or viscosities of elastomers were used.

In certain embodiments, the elastomer comprises an elastomer lumen that surrounds or encases the sliding element. In other embodiments, the elastomer is between the sliding element and the wall of the recess.

In certain embodiments the sliding element may be removable as a solitary element or in conjunction with the elastomer lumen. In other words, in certain embodiments, the sliding element is assembled into the plate and the silicone is molded to bond them together. In other embodiments, one could mold and bond the silicone onto the sliding element externally, and then push that component into the plate. In this case, it wouldn't be bonded to the plate. In another embodiment for an "unloaded," modular bone plate, a surgeon can insert either an elastic sliding element, anon-elastic locking element, or a non-locking element In certain embodiments, the elastic suspension of the sliding element in the plate is achieved by means of two or more spring elements that determine an amount of bi-directional translation of the sliding element relative to the plate in response to a load in a longitudinal direction of the plate.

In certain embodiments, the spring elements are comprised of discrete springs. In certain embodiments the spring elements are comprised of integrated springs formed by an elastic structure or material that is part of the sliding element.

In certain embodiments the spring elements are comprised of integrated springs formed by an elastic structure or material that is part of the plate segment adjacent to the sliding element.

In certain embodiments the spring elements are formed by an elastic material (elastomer) that is applied between the sliding element (shown as 3 in FIG. 12) and the plate (1).

In certain embodiments, the spring elements are formed by an elastic material (elastomer) lumen that encases or surrounds the sliding element. For example the elastorner is not between the walls of the recess and the edge of the sliding element but is also on top and below the sliding element, In one embodiment, a sliding element is suspended between two or more spring elements (such as shown, for example in FIG. 7). This configuration enables elastic displacement in two opposing directions. FIG. 7 shows an embodiment where two spring elements are integral to the sliding element. In another embodiment the spring elements may be separate from the sliding element. In another embodiment, the spring elements may be a combination of a separate spring element and an integral spring element. In other embodiments the spring element may be the elastomer or elastomer lumen. In other embodiments, there may be a combination of a spring element such as a separate spring and an elastomer. For example, one side of the sliding element could have a spring (separate or integral) and on the other side of the sliding element, the spring element could be an elastomer.

In certain embodiments, there may be a combination of discrete or integral spring elements with elastomeric spring elements. For example a discrete and/or integral spring element and the sliding element may be surrounded by an elastomer lumen. Or there may be a combination of a discrete or integral spring element and elastomeric material between the wall of the recess and the sliding element.

In certain embodiments, the elastic suspension of the sliding element in the plate is achieved by means of a spring element that holds each sliding element in a defined resting position, and that determines an amount of uni-directional translation of each sliding element relative to the plate in response to a load in a longitudinal direction of the plate.

In certain embodiments, the bone fracture plate is comprised of more than one (in certain embodiments more than one and in certain embodiments, more than two) through hole, each through hole having a sliding element and a spring element. In certain embodiments the bone fracture plate has all the same shaped and same material sliding elements and spring elements. In certain embodiments, the bone fracture plate has different shaped and/or different material sliding elements and/or different spring elements. For example, certain sections of the plate may have discrete spring elements where other sections of the plate may have spring elements integral to the sliding element and other sections may have elastomeric material spring elements or other areas of the plate may employ a combination of discrete, integral and/or elastic material spring elements.

In another embodiment, a single spring element is used to hold the sliding element in a defined resting position. This ensures a stable position of the sliding element during insertion of a bone screw. Subsequent loading of the fixation construct (such as what happens when a patient applies weight or force to the bone that has the fracture) initiates motion of the sliding element, whereby the onset of motion may be determined by the pre-load of the spring element. Upon load removal, the sliding element returns to its defined resting position.

In another embodiment, the sliding element may be partially or fully embedded in a low-friction layer, such as a polymer membrane. This arrangement reduces friction and wear between the sliding element and the plate.

In another embodiment, the sliding elements and corresponding fixation holes are configured in a staggered arrangement. See for example FIGS. 1, 3, and 10. Compared to sliding elements that are arranged along a straight line, this staggered fixation increases the stabilization of the fixation construct when subjected to torsional loading.

In certain embodiments one or more sliding elements extend past the bone-facing surface of the plate to elevate the plate body over the bone surface when the receiving hole is being compressed onto the bone surface with a non-locking bone screw, which, in conjunction with the elastic suspension of the sliding element, enables controlled relative motion between the plate and the bone surface, See FIG. 14.

In certain embodiments, the internal sliding element is at least partially enclosed within a cavity in the side of the plate. FIG. 11 shows the sliding element enclosed within a cavity in the side of the plate.

In another embodiment, the threaded receiving hole in the sliding element is conical. This enables positive locking of a correspondingly threaded conical screw head in the sliding element.

In another embodiment, the threaded receiving hole in the sliding element is cylindrical and is used in conjunction with bone screws that have the same thread outer diameter and thread pitch at the screw head and screw shaft. This has the advantage that the screw shaft is engaged in the threaded hole of the sliding element throughout screw insertion. This embodiment thereby prevents the screw head from being compressed against the sliding element. Ensuring that the screw head readily engages into the threaded hole of the sliding element also prevents pre-loading of the sliding element inside the bone plate.

Figure 3:
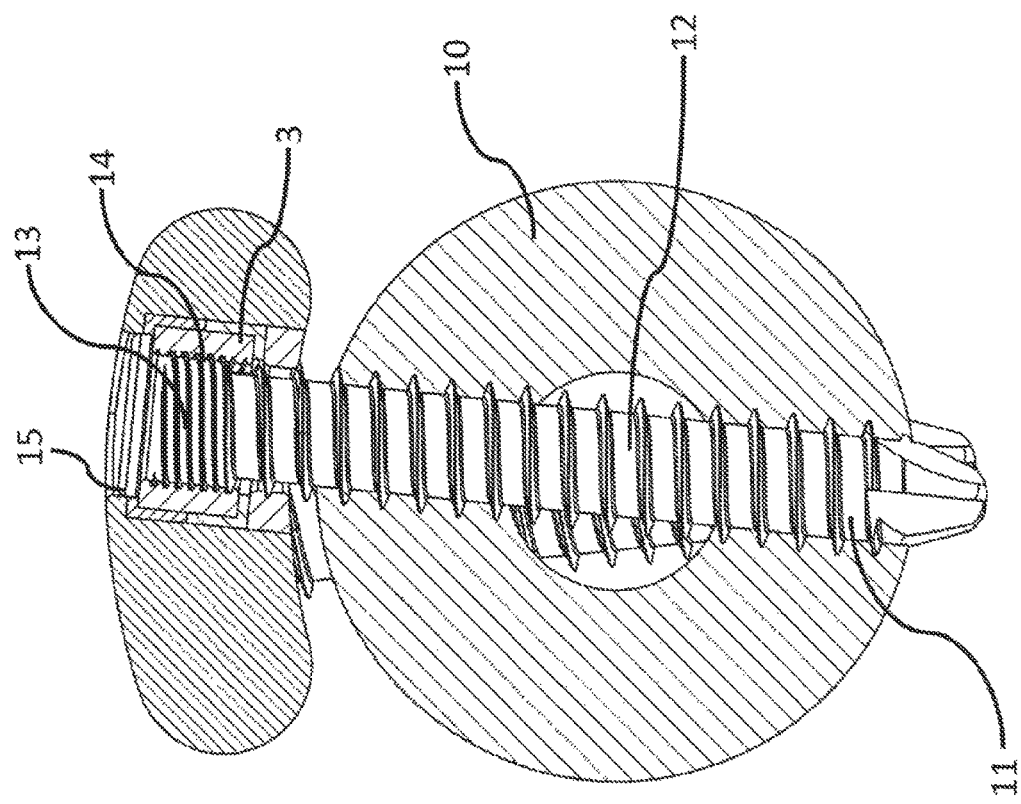
FIG. 3 is a transverse cross-sectional view of a bone plate shown affixed with a bone screw to a cylindrical bone member, in accordance with various embodiments.

In certain embodiments there are a plurality of bone screws (see FIGS. 3 and 9, for example). In certain embodiments, the device further comprises one or more non-collinear bone pegs with a threaded head and a smooth peg shaft (see FIG. 10, for example). In another embodiment, one or more sliding elements may be connected to a bone using pegs with threaded heads that positively engage with the threaded hole of sliding elements. The use of locking pegs in place of locking screws reduces the risk of pre-loading the sliding element inside the plate. To enhance the fixation strength, locking pegs may be inserted in a multi-planar configuration, wherein at least two threaded holes of sliding elements have central axes that are not collinear.

In certain embodiments, the plate incorporates threaded and/or non-threaded screw holes.

In another embodiment, sliding elements may only be located in a certain segment of the bone plate, while another segment of the bone plate has threaded or non-threaded holes (as used in the industry). In one embodiment, the spring elements and sliding elements are located in one segment of the plate, while another segment of the plate has threaded or non-threaded holes without spring elements and sliding elements. The bone plate segment with standard threaded holes or standard non-threaded holes without spring elements and sliding elements (as used in the industry) (referred to herein and in the claims as static receiving holes) allows compression and rigid fixation of the plate to the bone surface, whereas the bone segment with sliding elements/spring elements enables elastic fixation of a corresponding bone segment, which retains the ability to achieve interfragmentary motion in response to intermittent loading of the fixation construct. For example, on one side of the fracture, the bone plate may comprise elastic suspension using the spring elements and sliding elements whereas on the corresponding bone segment on the other side of the fracture, the bone plate comprises static receiving holes (and does not comprise elastic suspension). Also in certain embodiments sliding elements/spring elements and static receiving holes can be used together in the same section of the bone plate. For example, every other hole may be a static receiving hole (and the other holes are the elastic suspension through holes). In other embodiments, there is a mixture of elastic suspension (using sliding elements and spring elements) and static receiving holes, which mixture may be the same throughout the whole bone plate across the fracture. In other embodiments, the mixture of static receiving holes and elastic suspension may vary within the plate. For example, one side of the fracture may have more elastic suspension and few static receiving holes whereas on the other side of the fracture, there may be more static receiving holes than elastic suspension. In other words, different parts of the bone plate may use different combinations of each.

In another embodiment, sliding elements and one or more screw holes may be combined in the same plate segment. This allows temporary affixation of the plate to the bone surface using a standard non-locking screw to facilitate application of locking screws into sliding elements.

The present invention also provides methods of fixing a bone fracture using a flexible plate. In certain embodiments the method comprising: approximately aligning the fractured bone members; and applying a bone plate across the fracture with a plurality of bone fasteners that rigidly connect to receiving holes in a plurality of sliding elements that are elastically suspended in the bone plate. The sliding elements are configured to permit controlled translation parallel to the longitudinal axis of the bone plate, while substantially preventing displacement perpendicular to the longitudinal axis of the plate. The bone screw is rigidly fixed to the sliding elements without compressing the bone plate or sliding element onto a bone surface.

In certain embodiments the receiving holes are suspended to preferentially permit translation relative to the plate along the longitudinal axis of the plate while substantially constraining motion of the one or more receiving holes in a direction that is perpendicular to an upper or bone-facing surface of the bone plate.

In certain embodiments the spring elements act as elastic springs that suspend receiving holes in a neutral position relative to the plate in absence of load application and that enable controlled elastic translation of the receiving hole relative to the plate in response to load application.

In certain embodiments the flexible elements dampen the transmission of impact load between the plate and the bone member to enhance the stability of the fixation construct.

In certain embodiments the flexible elements enhance the distribution of load transfer between multiple fixation elements associated with a single bone segment. With standard static plates, typically one screw is loaded more than the rest since the alignment is not perfect. Using the elastic suspension of the present invention (elastically suspended sliding elements), the load is distributed across all of the screws since they are allowed to displace, and the elastic elements even out the loading.

In certain embodiments the flexible elements prevent at least in part direct contact between the receiving hole and the plate to reduce surface wear and material fatigue.

In certain embodiments the elastic suspension of two or more receiving holes and the plate is practiced on one side of a fracture, while the corresponding bone segment is attached to static receiving holes.

In certain embodiments the elastic suspension of two or more receiving holes and the plate is practiced on both sides of a fracture.

In certain embodiments the elastic suspension of two or more receiving holes and the plate provides for a substantial reduction in axial stiffness of the fixation constructs in the range of 40-90% compared to a bone plate construct with static receiving holes.

In certain embodiments one or more flexible elements contain a sensor to measure displacement, pressure, or load to capture the presence or magnitude of load transfer between a receiving element and the plate as a means for estimating the progression of fracture healing. For example, a sensor can be embedded to help determine when the bone is healed. For example, if the sensor measures displacement, then one would expect as the bone healed, the displacement of the parts would decrease with time. If the senor measured load, one would expect the load on the plate to diminish as the bone healed.

In certain embodiments the elastomer material comprises an elastomer lumen, and wherein the elastomer lumen of one or more of the flexible elements contains a means for energy generation to supply transient power to said sensor.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for flexible plate fixation of a bone fracture, the method comprising
approximately aligning the fractured bone members; and
applying a fixation construct across a fracture wherein the fixation construct comprises a bone plate having an upper surface and a bone-facing surface, the bone plate having one or more receiving holes and a plurality of elastically suspended sliding elements, the fixation comprising using a plurality of bone fasteners that connect the bone fasteners to the bone plate and wherein the bone fasteners are placed into the receiving holes into the sliding elements that are elastically suspended in the bone plate;
wherein the sliding elements are configured to permit controlled translation parallel to the longitudinal axis of the bone plate, while substantially preventing displacement perpendicular to the longitudinal axis of the bon plate, and wherein the bone fastener is rigidly fixed to the sliding elements without compressing the bone plate or sliding element onto a bone surface; and wherein
wherein the elastic suspension is provided by two or more spring elements.

2. The method of claim 1 wherein the elastic suspension of the two or more spring elements comprises an elastic material.

3. A method of claim 1, where said receiving holes are suspended to preferentially permit translation relative to the bone plate along the longitudinal axis of the plate while substantially constraining motion of the one or more receiving holes in a direction that is perpendicular to the upper or bone-facing surface of the bone plate.

4. A method of claim 1, whereby the spring elements act as elastic springs that suspend the receiving holes in a neutral position relative to the plate in absence of a load application and wherein the elastic swings enable controlled elastic translation of the receiving holes relative to the plate in response to the load application.

5. A method of claim 1, whereby the spring elements dampen transmission of an impact load between the bone plate and the bone member to enhance stability of the fixation construct.

6. A method of claim 1, whereby the spring elements enhance distribution of load transfer between multiple bone fasteners associated with a single bone segment.

7. A method of claim 1, whereby the spring elements prevent at least in part direct contact between the receiving hole and the bone plate to reduce surface wear and material fatigue.

8. A method of claim 1, wherein the elastic suspension of two or more receiving holes and the plate is practiced on one side of a fracture, while the corresponding bone segment is attached to static receiving holes.

9. A method of claim 1, wherein the elastic suspension of two or more receiving holes and the bone plate is practiced on both sides of a fracture.

10. A method of claim 1, wherein the elastic suspension of two or more receiving holes and the bone plate reduces axial stiffness of the fixation constructs by about 40-90% compared to a bone plate construct having static receiving holes.

11. A method of claim 1, wherein one or more spring elements contain a sensor to measure displacement, pressure, or load to capture a presence or magnitude of load transfer between the sensor and the bone plate as a means for estimating the progression of fracture healing.

12. A method of claim 2, wherein the elastic material comprises an elastomer lumen, and wherein the elastomer lumen of one or more of the spring elements contains a means for energy generation to supply transient power to said sensor.

13. A method of claim 2, wherein the elastic material comprises an elastomer lumen, and wherein the elastomer lumen is configured to permit a timed release of pharmacological substances.

14. A method of claim 2, wherein the elastic material comprises silicone.

15. A method of claim 2, wherein the elastic material is bonded to the surface of the bone plate and/or sliding element.

* * * * *

UNITED STATES PATENT AND TRADEMARK OFFICE
CERTIFICATE OF CORRECTION

PATENT NO. : 9,700,361 B2
APPLICATION NO. : 15/047702
DATED : July 11, 2017
INVENTOR(S) : Bottlang et al.

It is certified that error appears in the above-identified patent and that said Letters Patent is hereby corrected as shown below:

On the Title Page

On page 4, in Column 2, under "Other Publications", Line 2, delete "Stabilzed" and insert --Stabilized-- therefor On page 4, in Column 2, under "Other Publications", Line 15, delete "28," and insert --25,-- therefor In the Claims In Column 11, Line 47, in Claim 1, after "comprising", insert --:--

In Column 11, Line 62, in Claim 1, delete "bon" and insert --bone-- therefor

In Column 12, Line 3, in Claim 1, after "and", delete "wherein"

In Column 12, Line 6, in Claim 2, after "claim 1", insert --,--

In Column 12, Line 9, in Claim 3, delete "A" and insert --The-- therefor

In Column 12, Line 14, in Claim 4, delete "A" and insert --The-- therefor

In Column 12, Line 17, in Claim 4, delete "swings" and insert --springs-- therefor In Column 12, Line 20, in Claim 5, delete "A" and insert --The-- therefor In Column 12, Line 24, in Claim 6, delete "A" and insert --The-- therefor In Column 12, Line 27, in Claim 7, delete "A" and insert --The-- therefor Signed and Sealed this
Eighteenth Day of September, 2018

Andrei Iancu
*Director of the United States Patent and Trademark Office*

CERTIFICATE OF CORRECTION (continued)
U.S. Pat. No. 9,700,361 B2

In Column 12, Line 31, in Claim 8, delete "A" and insert --The-- therefor

In Column 12, Line 35, in Claim 9, delete "A" and insert --The-- therefor

In Column 12, Line 38, in Claim 10, delete "A" and insert --The-- therefor

In Column 12, Line 43, in Claim 11, delete "A" and insert --The-- therefor

In Column 12, Line 48, in Claim 12, delete "A" and insert --The-- therefor

In Column 12, Line 53, in Claim 13, delete "A" and insert --The-- therefor

In Column 12, Line 57, in Claim 14, delete "A" and insert --The-- therefor

In Column 12, Line 59, in Claim 15, delete "A" and insert --The-- therefor